(12) United States Patent
Kolberg et al.

(10) Patent No.: US 9,468,384 B2
(45) Date of Patent: Oct. 18, 2016

(54) IMPLANTABLE ELECTRODE LEAD

(75) Inventors: Gernot Kolberg, Berlin (DE); Jochen Palm, Mahlow (DE); Klaus Bartels, Berlin (DE)

(73) Assignee: BIOTRONIK SE & Co. KG, Berlin (DE)

( * ) Notice: Subject to any disclaimer, the term of this patent is extended or adjusted under 35 U.S.C. 154(b) by 130 days.

(21) Appl. No.: 13/338,433

(22) Filed: Dec. 28, 2011

(65) Prior Publication Data

US 2012/0184836 A1 Jul. 19, 2012

Related U.S. Application Data

(60) Provisional application No. 61/432,212, filed on Jan. 13, 2011.

(51) Int. Cl.
*A61B 1/00* (2006.01)
*A61B 5/04* (2006.01)
*A61N 1/05* (2006.01)
*A61B 5/00* (2006.01)
*A61N 1/00* (2006.01)

(52) U.S. Cl.
CPC .............. *A61B 5/04* (2013.01); *A61B 5/6846* (2013.01); *A61N 1/05* (2013.01); *A61B 2562/0209* (2013.01); *A61B 2562/16* (2013.01); *A61B 2562/187* (2013.01); *A61B 2562/222* (2013.01)

(58) Field of Classification Search
CPC ............... A61B 1/0055; A61B 2017/2905; A61B 2017/2927; A61B 2017/2929; A61M 2025/0161
USPC ........ 600/372–375, 377, 393–394, 508–510; 607/115–116, 119, 122–123, 126–130
See application file for complete search history.

(56) References Cited

U.S. PATENT DOCUMENTS

| 3,190,286 | A | * | 6/1965 | Stokes | A61B 1/00165 138/120 |
| 3,266,059 | A | * | 8/1966 | Stelle | B25J 9/06 138/120 |
| 4,651,718 | A | * | 3/1987 | Collins et al. | 600/142 |
| 4,700,693 | A | * | 10/1987 | Lia et al. | 600/141 |
| 4,773,395 | A | * | 9/1988 | Suzuki et al. | 600/142 |
| 5,005,558 | A | * | 4/1991 | Aomori | A61B 1/0055 600/141 |
| 5,329,923 | A | * | 7/1994 | Lundquist | 600/373 |

(Continued)

FOREIGN PATENT DOCUMENTS

WO 2004/110542 12/2004

OTHER PUBLICATIONS

European Search Report and Notes to the European Search Report on European Patent Application No. EP 11 19 4024, dated May 24, 2012 (6 pages).

*Primary Examiner* — Joseph Stoklosa
*Assistant Examiner* — Brian M Antiskay
(74) *Attorney, Agent, or Firm* — Buchanan Ingersoll & Rooney PC

(57) ABSTRACT

An implantable electrode lead for transmitting electrical impulses to excitable bodily tissue and/or for transmitting electrical signals tapped at bodily tissue to a detection unit. The electrode lead including a distal electrode, a proximal electrode connector, and an electrode supply lead which connects the electrode, or each electrode, to the electrode connector, or each electrode connector, and extends in a lead body, wherein the lead body includes a hinged alignment of hard elements.

25 Claims, 8 Drawing Sheets

(56) References Cited

U.S. PATENT DOCUMENTS

| | | | |
|---|---|---|---|
| 5,448,989 A * | 9/1995 | Heckele | 600/142 |
| 5,681,263 A * | 10/1997 | Flesch | A61B 1/0055 600/139 |
| 6,374,143 B1 * | 4/2002 | Berrang et al. | 607/137 |
| 7,561,906 B2 * | 7/2009 | Atalar | A61N 1/05 600/374 |
| 7,680,544 B1 | 3/2010 | Conger | |
| 8,588,934 B2 * | 11/2013 | Lloyd | A61B 5/0422 607/116 |
| 8,798,767 B2 * | 8/2014 | Foster | 600/373 |
| 2006/0041293 A1 * | 2/2006 | Mehdizadeh et al. | 607/116 |

* cited by examiner

- Prior Art -

- Prior Art -

- Prior Art -

IMPLANTABLE ELECTRODE LEAD

RELATED APPLICATION

This patent application claims the benefit of U.S. Provisional Patent Application No. 61/432,212, filed on Jan. 13, 2011, which is hereby incorporated by reference in its entirety.

TECHNICAL FIELD

The present disclosure relates to an implantable electrode lead for transmitting electrical impulses to excitable bodily tissue and/or for transmitting electrical signals tapped at bodily tissue to a detection unit. The implantable electrode lead generally includes a distal electrode, a proximal electrode connector, and an electrode lead which connects the electrode or each electrode, or is used to transmit electrical shocks or to control sensors, and which extends in a lead body.

BACKGROUND

Such electrode leads, which are used to transmit (e.g., stimulation impulses from cardiac pacemakers to the heart, or possibly action potentials that occur at the heart to the cardiac pacemaker, or the shock impulses of an implanted cardioverter to the heart, and possibly action potentials tapped at the heart to the cardioverter, or which are used to stimulate regions of the brain or nerves, or to transmit electrical signals tapped at the brain/nerve regions to a detection and evaluation device, are used on a large scale for clinical applications.

Of the numerous fields of application for electrode leads, there are a few in which they are exposed, at least in subsections, to high mechanical loads which can impair the functionality or even disable the electrode lead entirely during long-term use. Examples thereof include, but are not limited to, cardiac pacemaker electrode leads, one or more supply leads between an implanted control device and one or more implantable sensors, and ICD electrodes that have one or more very large areas for the application of very high current pulses into the tissue over a large surface area.

First, excess length of the electrode is enclosed in the pacemaker pocket. A tenacious connective-tissue membrane grows around the structure. At the points at which the electrode comes in contact with the housing or intersects other electrode sections, high pressure loads can be placed on the lead body since the connective tissue growing around it does not allow the electrode to yield. Proceeding there from, the electrode extends generally through the region between the clavicle and the first coastal arch. If the electrode is in an unfavorable position, it can become pinched.

Extensive developmental work in the past resulted in various possible solutions to this problem. Electrode leads are designed to be highly flexible. The hard materials, such as, for example, metal, that are used for the supply leads are configured to be highly flexible. Wires are wound into coils or are woven very thinly to form ropes. Plastics that are soft and as elastic as possible are used as insulators that offer the least possible resistance to the movements of the electrode.

The known solutions have not proven to be entirely satisfactory in practice. For example, if radial pressure is applied, the insulation material yields in a manner such that the pressure ultimately acts on the supply leads. Moreover, the pinching of the insulation material stresses the plastic. The stress can cause the material to degrade or directly cause it to yield mechanically. The insulation wears off, bursts, or degrades. Initially, the insulation is breached. Bodily fluid can penetrate the electrode and close electrolyte bridges between the leads. Shunts or short circuits can negatively affect therapy. In the worst case, however, the supply leads break and therapy fails. Furthermore, it can not be ruled out that a broken electrode body will cause further damage.

The problems addressed by the present description are therefore that of providing an improved electrode lead which is more resistant to substantially radially acting forces and friction, at least in certain sections in particular, while remaining as flexible as necessary.

The present inventive disclosure is directed toward overcoming one or more of the above-identified problems.

SUMMARY

One or more problems are solved by an electrode lead having the features of the independent claim(s). Further advantageous developments are the subject matter of the dependent claims.

In this context, the term "hard elements" refers to separate elements or even delimitable sections in the longitudinal extension of a lead body, which are extremely resistant ("hard") to forces that act radially or obliquely to the longitudinal axis of the electrode lead and are short relative to the total length of the electrode lead. According to the present disclosure, at least those sections in the longitudinal extension of an electrode lead that are typically exposed to strong mechanical loads of that type are designed to be particularly resistant.

An electrode lead designed on the basis of the solution according to the present description is substantially more stable against mechanical loads to which it is exposed in practical application. The radial compression and flexing forces being applied are absorbed here by an additional shield, namely, the hard elements. The functional components, i.e., the supply lead, which is comprised of rope or coil or combinations thereof, and the insulators, which are comprised of plastic, are limited in terms of their actual function (namely, to conduct or insulate). In conventional electrodes, due to the radial forces acting thereon, these functional elements had to withstand various loads, such as, for example, torsional moments, tensile forces, flexing forces, and friction. An optimal embodiment of the solution according to the present description also provides permanent protection against unwanted movements of the electrode body. For example, relative motions between the supply lead and the insulation can be minimized.

Further aspects of embodiments of the present description are the following, which represents a non-exhaustive list:
1. Materials for at least a portion of the hard elements can be:
   Metal: Platinum, tantalum, iridium, palladium, steel, MP35N, gold, etc.
   Ceramic: Al2O3, ZrO2, TiO2, MgO, ZnO, aluminum titanate (Al2O3+TiO2), barium titanate (BaO+TiO2), silicon carbide (SiC), beryllium oxide (BeO), aluminum nitride (AlN), hafnium carbide (HfC), tantalum carbide (TaC), titanium nitride (TiN), boron nitride (BN), boron carbide (B4C), tungsten carbide (WC), silicon nitride (Si3N4), etc.
   Glass:
   Plastic: PEEK, silicone, various copolymers, polyimide, PA, high-density polyethylene, polysulphone, or variants of the aforementioned plastics filled with fibers or nanoparticles, etc.

2. The hard elements alternate with elastic elements (sections).
3. The quality of the elements changes along the extension of the electrode.
4. The hard elements of the chain are interconnected by an elastic material.
5. The elastic material is applied by extrusion or coating or injection molding of the chain.
6. The elements of the chain are enclosed in an elastic material.
7. The supply lead body is enclosed in an abrasion-resistant tube.
8. At least one coil or one reinforcing wire extends in the core of the chain, e.g., in a lumen
9. At least one rope extends in the core of the chain.
10. The coil(s) or the rope(s) or combinations thereof are insulated from one another and/or from the chain.
11. The openings are asymmetrical (a core lumen need not be provided).
12. The elements of the chain are insulators.
13. The elements of the chain are semiconductors.
14. The elements of the chain are conductive.
15. The shape of the elements changes depending on the function.
16. Individual elements have different lengths.
17. Individual elements have different diameters.
18. Individuals elements of the chain are designed as a ring electrode or can accommodate a ring electrode.
19. Individuals elements of the chain are designed as sensors or can accommodate sensors.
20. Individuals elements of the chain are designed as coils or can accommodate coils.
21. Individuals elements of the chain are designed as capacitors or can accommodate capacitors.
22. Individual elements of the chain contain electronic components, analog or digital circuits or combinations thereof, accumulators, batteries, antenna, transmitters, or receivers or combinations thereof.
23. Individual elements of the chain are designed as fixation elements or can accommodate fixation elements, which are used to affix the electrode at the intended location thereof.
24. The elements have openings for the eccentrically extending supply leads, which define the path in which they extend.
25. The eccentrically extending supply leads are disposed in parallel to the axis of the electrode body.
26. The eccentrically extending supply leads are coiled around the axis of the electrode body.
27. The eccentrically extending supply leads are coiled around the axis of the electrode lead, wherein the slope of the coil changes along the electrode length, reverses (winds in the opposite direction), or approaches infinity, i.e., extends in parallel.
28. The end faces (contact surfaces) of the elements to the adjacent elements are designed in a manner (e.g., flattened) such that the chain is easier to bend.
29. The contact surfaces of the elements are designed in a manner such that, if bent, the minimum bending radius of the chain is limited.
30. The elements are designed in a manner such that the degree of freedom of motion toward the adjacent elements is limited. Elements perform joint functions (i.e., the chain no longer bends in all directions at this transition of the chain elements), wherein the elements designed as joints are designed such that they can absorb tensile forces (a so-called "reaching behind").
31. The plane of motion toward the subsequent element is rotated by an angle, e.g., of approximately 90°.
32. The eccentrically extending supply leads are guided in the joint plane from one element to the next (thereby minimizing the motion of the lead relative to the element).
33. The elements are injection molded onto a tube or are extruded thereon.
34. The above-described elements are separated from each other by special elements which function as joints.
35. The elements are interconnected by integrated joints.
36. The elements are made from a tube.
37. The elements are aligned in a row, e.g., overlapped in a shingled formation.
38. The sections of the tube are interconnected.
39. The tube is made from one continuous piece, in particular, using, for example, laser-beam cutting.
40. The type of chain changes along the extension of the electrode. Segments of the electrode body are designed as chains and others use traditional design principles of the electrode body.

Various other objects, aspects and advantages of the present inventive disclosure can be obtained from a study of the specification, the drawings, and the appended claims.

DESCRIPTION OF DRAWINGS

Advantages and useful features of the present description also result from the descriptive examples that follow, with reference to the figures. They show.

DETAILED DESCRIPTION

Figure 1:
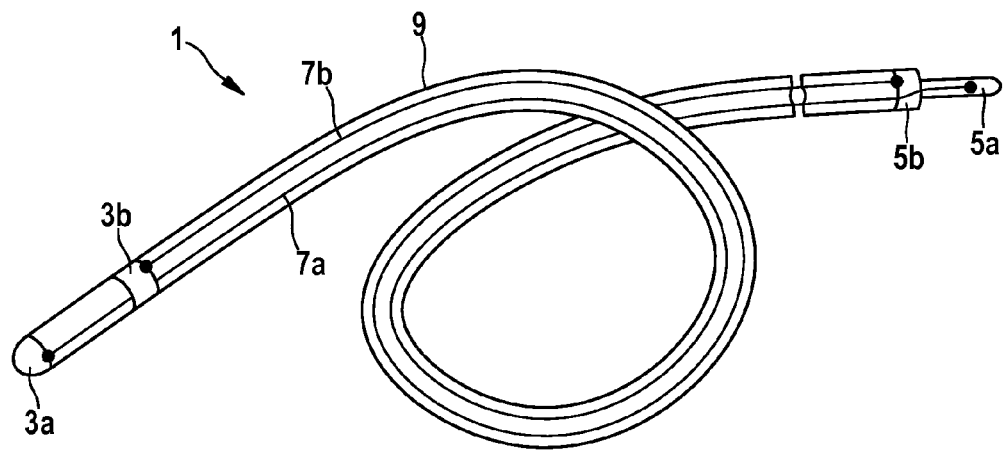
FIG. 1 is a schematic representation of a conventional implantable electrode lead.

In the description of the various Figures that follow, similar reference numerals are used for identical or identically-acting parts or sections, and previous descriptions are not repeated for subsequent Figures provided they refer to such parts and no special circumstances exist. Embodiments of the present disclosure are illustrated by way of example, and not by way of limitation, in the Figures.

FIG. 1 is a schematic depiction of a bipolar electrode lead 1, on the distal end of which a point electrode 3*a* and a ring electrode 3*b* are disposed. Two corresponding electrode contacts 5*a* and 5*b* are provided on the proximal end thereof, each being connected to the respective associated electrode 3*a*, 3*b* by a first and a second supply lead 7*a*, 7*b*, respectively. The electrodes, 3*a*, 3*b*, electrode contacts, 5*a*, 5*b*, and supply leads 7*a*, 7*b* are accommodated on or in a lead body 9, which typically comprises multiple layers.

Figure 2:
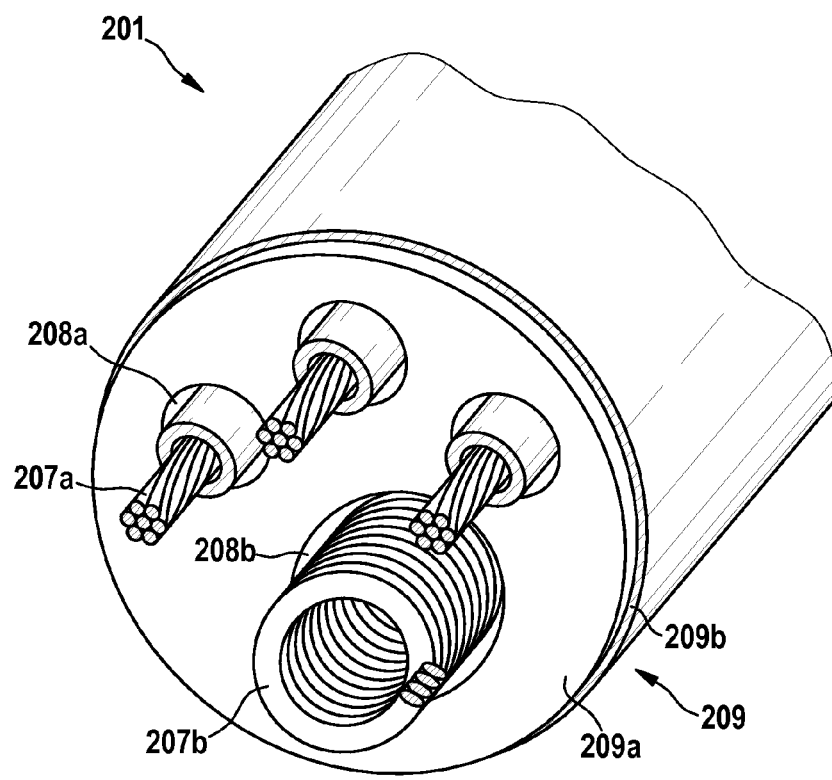
FIG. 2 shows, in a perspective sectional view, an example of a highly developed electrode lead comprising a plurality of supply leads accommodated in one lead body.

FIG. 2 shows, in a perspective sectional view having various cutting planes, an electrode lead 201, in the case of which three lumina 208*a* having a smaller diameter and an additional lumen 208*b* having a larger diameter are provided in an inner tube 209*a*, which is the core of a supply lead body 209. Each of the smaller lumina 208*a* contains an electrode supply lead 207*a* having a rope structure which is provided with an insulating jacket comprised of, e.g., PTFE, ETFE or PI, and which is not labeled separately. A supply lead coil 207*b*, which can accommodate a guide wire during implantation to reinforce the electrode lead, extends in larger lumen 208*b*. To improve the sliding and wear properties of lead body 209, it is provided with an outer shell 209*b* which positively influences these properties.

Figure 3:
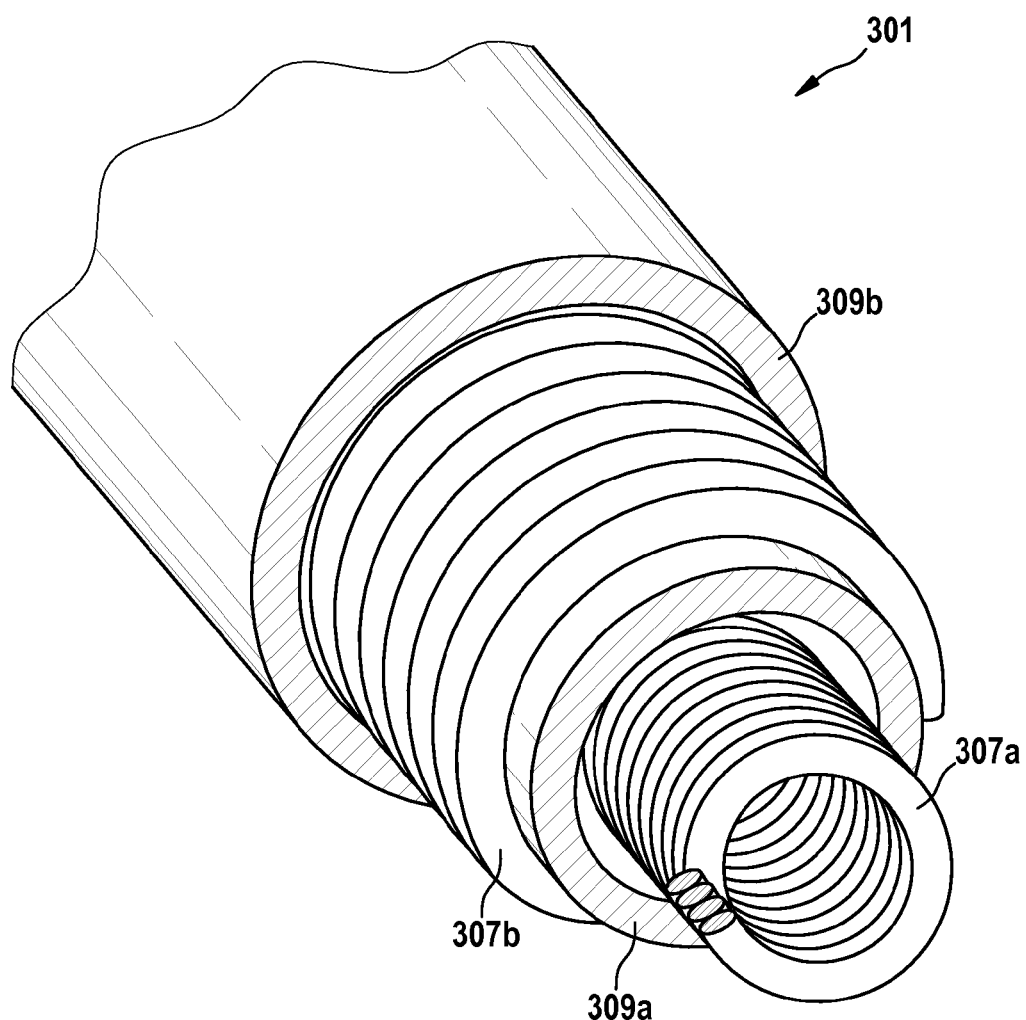
FIG. 3 shows, in a perspective sectional view, a further highly developed electrode lead comprising a plurality of supply leads in a coaxial arrangement.

FIG. 3 shows a further embodiment of an implantable electrode lead, in the case of which an inner coil 307*a*, which comprises a plurality of wound individual wires, is disposed, as the first electrode supply lead (or the first group of supply leads), coaxially to an outer coil 307*b*, which likewise comprises a plurality of wound individual wires (and which can likewise form a group of electrode supply leads). A silicone tube 309*a* is provided between the inner coil 307*a* and the outer coil 307*b*, and the outer coil 307*b* is enclosed by a further insulating tube 309*b* which can likewise be comprised of, for example, silicone or a polyurethane or a copolymer. A combination of a plurality of tubes can also be used here.

Figure 4A:
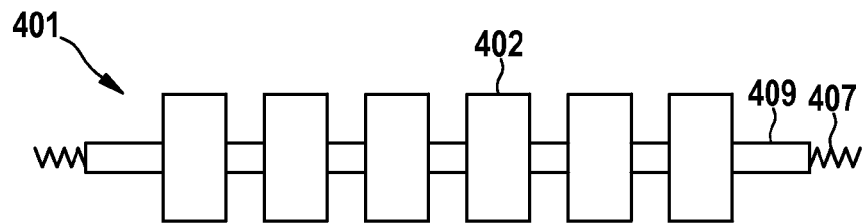
FIGS. 4A-4B and FIGS. 5A-5B each show schematic depictions of an electrode lead designed according to the present description, in a side view.
Figure 4B:
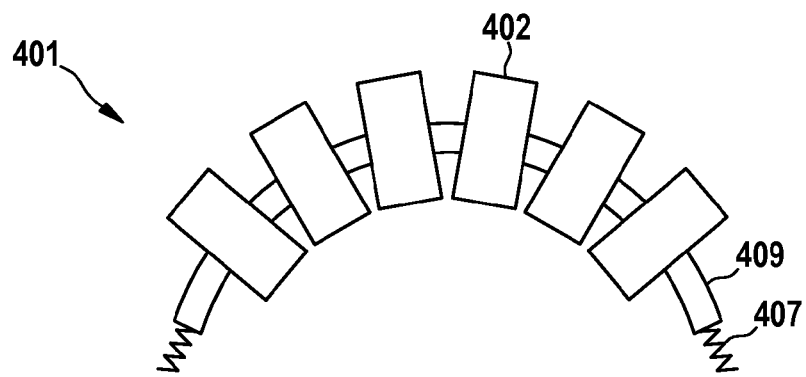
Figure 5A:
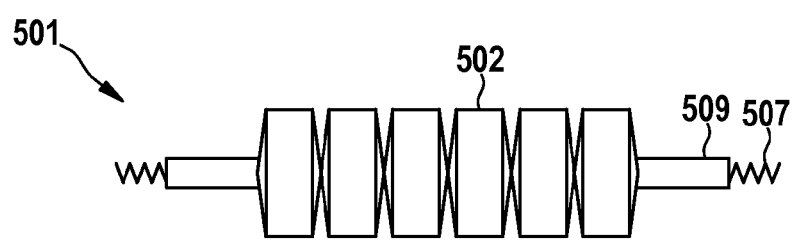
Figure 5B:
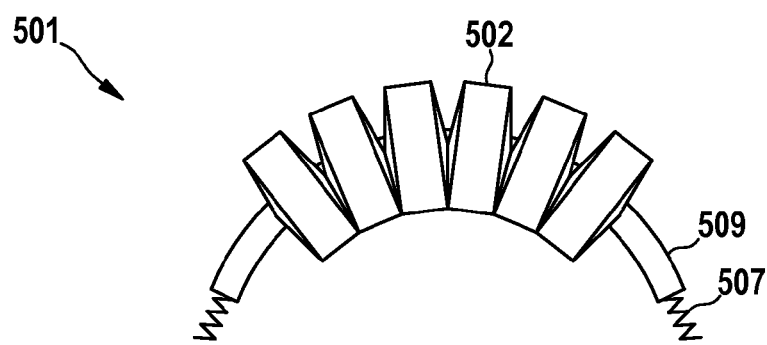

FIGS. 4A and 4B show, schematically in a side view, a section of an electrode lead 401 designed according to the present description, in which a group of disk-shaped, hard, closely interspaced elements 402 is disposed, as protection against strong mechanical loads, on a lead body 409 which contains an electrode supply lead 407. The elements 402 are spaced such that the electrode lead 401 can bend in the stated section (see FIG. 4B). The minimal bending radius is generally determined by the spaced distance of the hard elements 402. FIGS. 5A and 5B show a similar electrode lead 501 which differs from that shown in FIGS. 4A-4B only by the tight alignment of protective hard elements 502 on lead body 509, and by the shape of these elements 502. Both end faces of the elements 502 are conical (and therefore the overall shape is approximately disk-shaped), thereby enabling the electrode lead 501 to bend in the stated section (see FIG. 5B) despite the tight alignment. The minimal bending radius is determined by the cone angle of the end faces of hard elements 502.

Figure 6A:
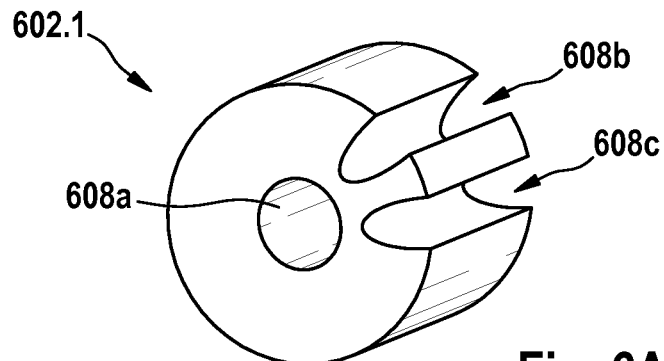
FIGS. 6A-6C each show, in schematic perspective sectional views, a hard element of an embodiment of the electrode lead according to the present description.
Figure 6B:
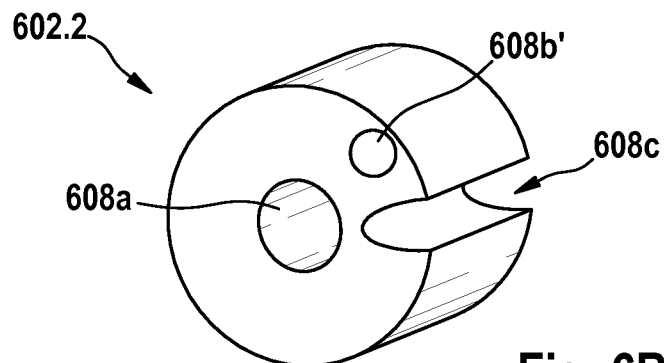
Figure 6C:
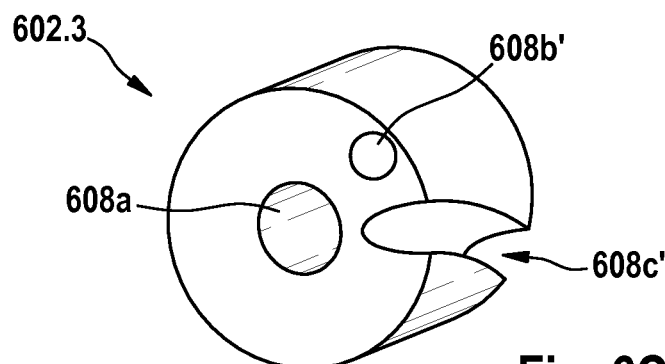

FIGS. 6A-6C show perspective depictions of various shaped hard elements 602.1, 602.2 and 602.3. All embodiments have the main shape of a cylinder or a disk, and a central lumen 608*a* for a first electrode supply lead, which is not depicted. Hard element 602.1, as shown in FIG. 6A, also comprises two radial recesses 608*b* and 608*c*, in which further electrode supply leads can be placed. In the case of hard element 602.2, shown in FIG. 6B, and 602.3, shown in FIG. 6C, a second inner lumen 608*b'* is provided in place of one radially open recess 608*b*. Moreover, in the case of hard element 602.3, shown in FIG. 6C, remaining recess 608*c'* is curved, as, for example, a section of a coil, and so when a plurality of similarly shaped elements are disposed in a row, a coiled extension of this recess or groove results and can be used to determine an identical coiled extension of an electrode supply lead placed therein.

In the case of hard elements 602.1, 602.2, 602.3 shown in FIGS. 6A-6C, central lumen 608*a* can accommodate, for example, a guide wire, a tube, a coiled electrode supply lead, or a rope-like electrode supply lead. Supply leads that are rope-like and extend separately or are designed as thin coils can be accommodated in the recesses, which are accessible from the outside, or in further lumina. The recesses, which are accessible from the outside, can be formed subsequently in the electrode lead. This is not an option, however, when disposed in smaller lumen 608*b'*, but the rope-shaped or coiled supply lead extending therein is better insulated against the surroundings. Structures formed in this manner provide a certain amount of protection for the supply lead if they are intended to be guided under a ring electrode or a shock coil.

Figure 7:
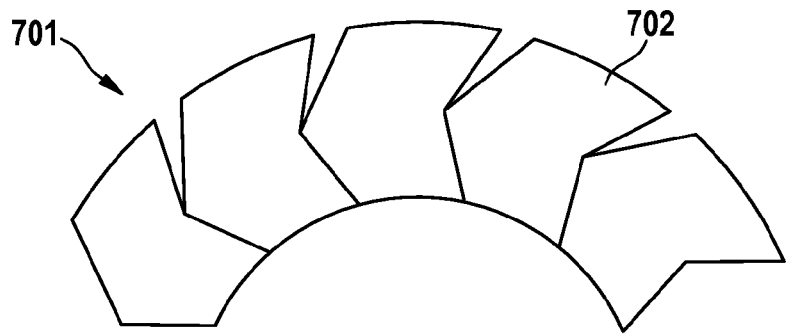
FIG. 7 is a schematic side view of a section of a further electrode lead according to the present description.

FIG. 7 shows, in a schematic side view, as another embodiment of the present description, an electrode lead 701 in a bent state. The electrode lead 701 likewise comprises hard elements 702 aligned in a section which is exposed to special mechanical loads. The main shape of the hard elements 702 is cylindrical, having the one end face of which has a triangularly notched cross section, and the other end face of which has a projecting contour that matches the shape of the aforementioned triangular notch. Similar to the embodiment shown in FIGS. 5A and 5B, this shape of the hard elements also enables the electrode lead to bend with a predetermined minimum radius.

Figure 8:
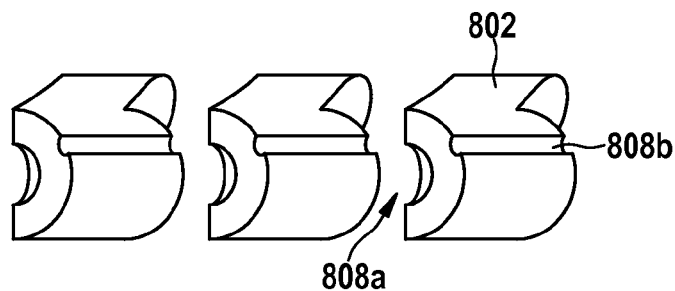
FIG. 8 are perspective depictions of three hard elements of an embodiment of the electrode lead shown in FIG. 7.

FIG. 8 shows, as an embodiment of the design shown in FIG. 7, three hard elements 802 which are adjacent to one another and are detached from the actual lead body, in the case of which a central lumen 808*a* as well as a laterally offset, smaller lumen 808*b* are provided in each hard element 802. The second lumen 808*b* is situated close to a plane of symmetry of the hard elements 802, which simultaneously determines the plane—which is orthogonal thereto—in which the electrode lead provided with such elements 802 can bend, thereby ensuring that the rope extending there through is neither substantially stretched nor substantially compressed when the electrode lead bends. As a result, relative movements between the electrode supply lead accommodated in the lumen and the protective elements are largely prevented.

Figure 9:
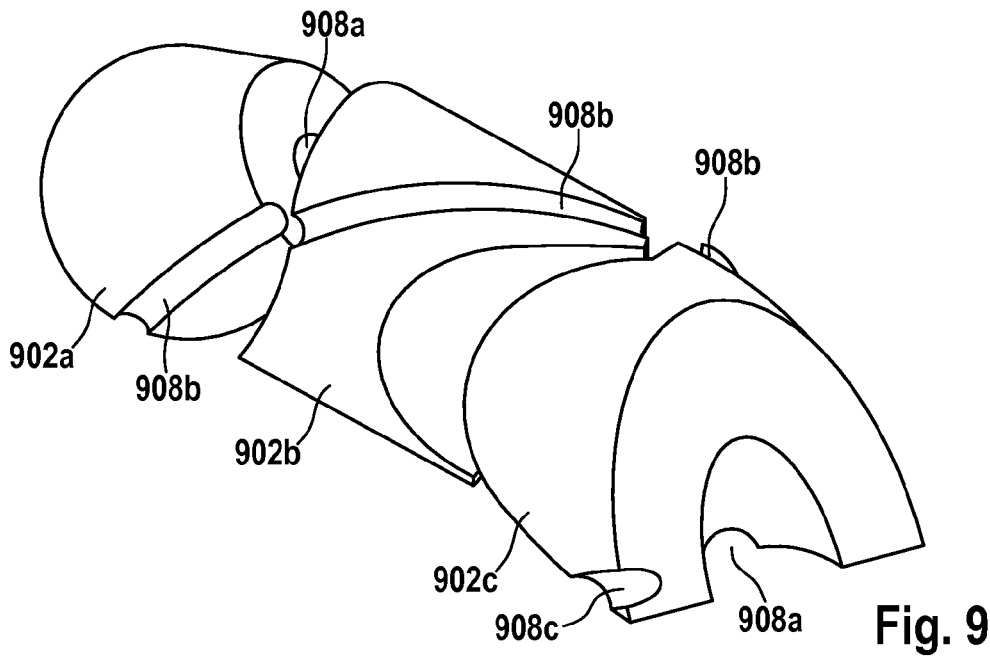
FIG. 9 is a perspective depiction of adjacently disposed, hard elements of a further electrode lead according to the present description.

Another embodiment of the design principle depicted in sketches in FIGS. 7 and 8 is shown in FIG. 9 in the form of a group of hard elements 902*a*, 902*b*, 902*c*. In addition to a central lumen 908*a*, these elements each comprise two radial grooves 908*b* and 908*c* which do not extend parallel to the central lumen 908*a* (and therefore in the longitudinal direction of the particular element), but rather obliquely thereto. According to this embodiment, a group of hard elements is shaped—being coordinated with one another—such that the plane of symmetry of the notch on an end face is oriented orthogonally to the orientation of the notch on the other end face, simultaneously ensuring a continuous, coiled extension of radial grooves 908*b*, 908*c* over all elements in the row. Thus, the electrode body can bend in any direction even if only three chain elements are aligned.

Figure 10:
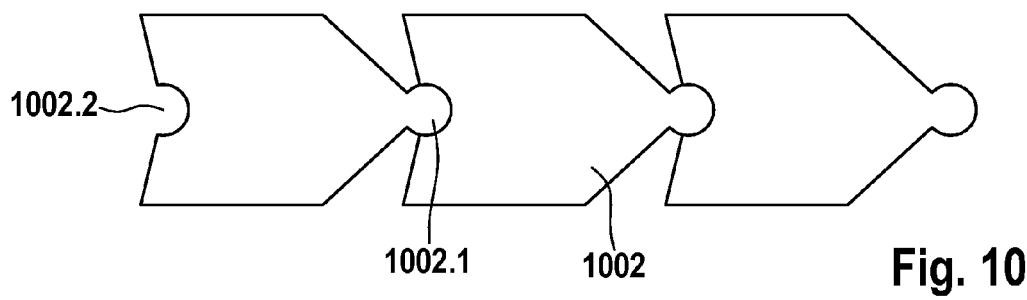
FIG. 10 is a schematic side view of a further embodiment of the present description.

FIG. 10 shows, schematically, as another embodiment of the present description, a group of three hard elements 1002 which are to be applied onto or in an electrode lead body. The hard elements 1002 are characterized by a spherical or circular disk-shaped projection 1002.1 on the one end face, which is otherwise, for example, conical in shape, and a matching ball socket 1002.2 on the other end face which has a shallower slope and is likewise conical in shape. In the installed state, the balls or circular disks 1002.1 and ball sockets and circular disk sockets 1002.2 form a rotationally symmetrical joint connection between the hard elements 1002, thereby enabling an electrode lead equipped therewith to bend in any direction.

Figure 11:
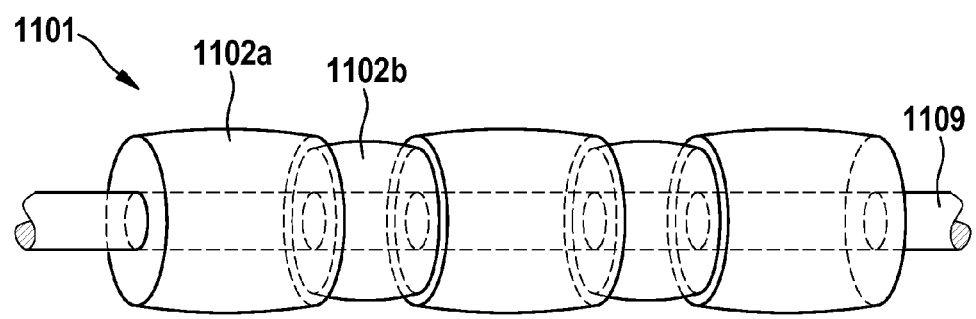
FIG. 11 is a schematic perspective depiction of a section of a further electrode lead according to the present description.

As an alternative to the joint connection sketched in FIG. 10, FIG. 11 shows another solution for ensuring high bendability in the form of an electrode lead 1101. Lead 1101 comprises a lead body 1109 which typically is comprised of an elastic plastic material, and the internal components (special supply leads) of which are not depicted here. First hard elements 1102a and second hard elements 1102b are slid onto lead body 1109 in alternation. The depiction in FIG. 11 is purely schematic, although it illustrates how first hard elements 1102a have a cylindrical to barrel-type main shape and both of their end faces have a concave shape, while second hard elements 1102b have an approximately spherical main shape and engage the first hard elements 1102a in the concave end faces. This engagement also results in the formation of a type of ball joint, thereby enabling the electrode lead 1101 to bend in all planes.

Figure 12:
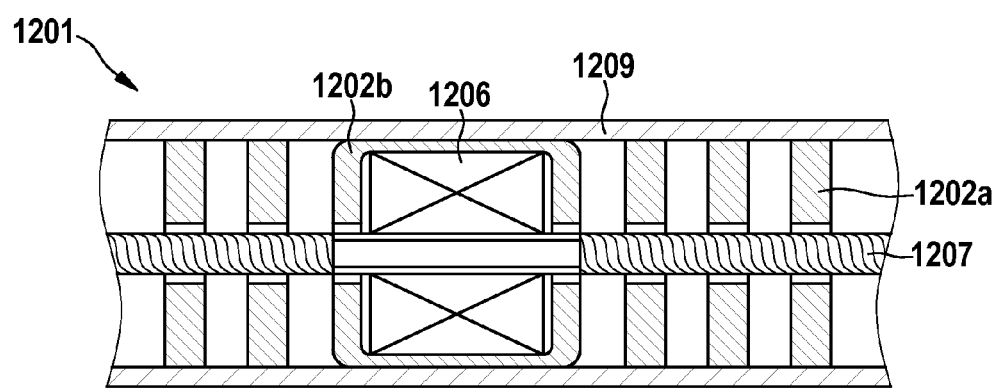
FIG. 12 is a schematic longitudinal sectional view of a further embodiment of the present description, in which a hard element also performs an electrical function.

FIG. 12 shows, in a schematic longitudinal cross-sectional view, another electrode lead 1201 according to the present description, which comprises an electrode supply lead 1207, a group of first hard elements 1202a which protect the supply lead 1207, and a lead body 1209 which is situated on the outside in this case and encloses supply lead 1207 with hard elements 1202a placed thereon. A unique feature of the embodiment shown in FIG. 12 is that an individual hard element 1202b of a second type is inserted between disk-shaped, hard elements 1202a. This different element 1202b is generally drum-shaped and contains in the interior thereof a coil 1206 which is an additional electrical component and is connected mechanically and electrically to central electrode supply lead 1207. This connection can be configured as an electrical series circuit, thereby increasing the inductance of the electrode supply lead 1207. The drum-shaped housing of hard element 1202b is rotatably supported on the electrode supply lead 1207, thereby enabling the lead body 1209 to rotate relative to the electrode supply lead 1207 with the coil 1206 securely placed thereon and preventing torsional stresses from forming during use of the electrode lead 1201.

Figure 13:
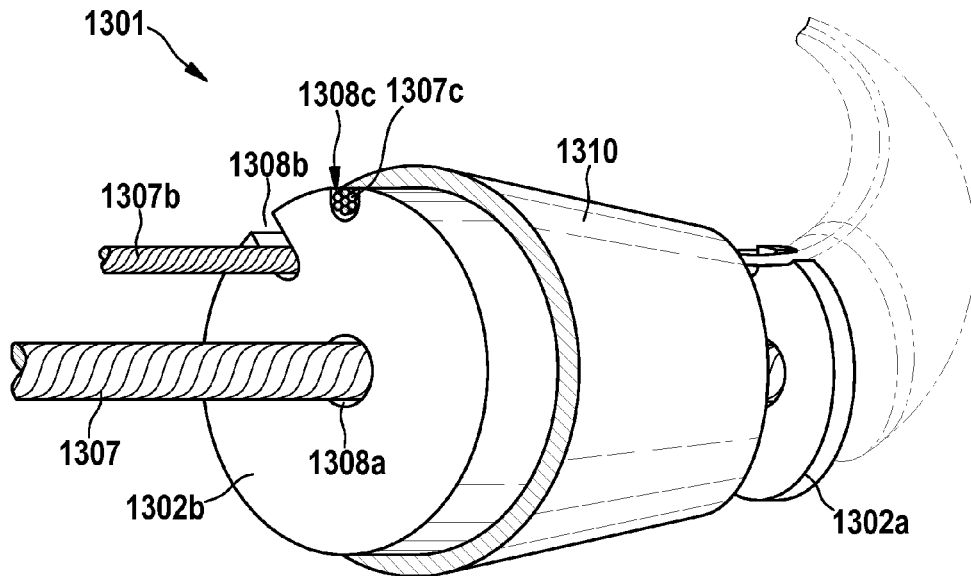
FIG. 13 is a perspective view of a further embodiment of the present description.

FIG. 13 shows, as another embodiment of the present description, an electrode lead 1301 which is protected by hard elements 1302a, the design of which is similar to the embodiment depicted in FIG. 6A. Electrode lead 1301 comprises a ring electrode 1310 which is situated as a ring around the outer circumference of a different hard element 1302b. In the case of element 1302b, second radial recess 1308c is reduced in size such that a supply lead 1307c accommodated therein is forced into mechanical and electrical contact with the inner wall of ring electrode 1310, which is thereby connected electrically to supply lead 1307c. The connection can also be fixed using a welding point or other known means.

Figure 14A:
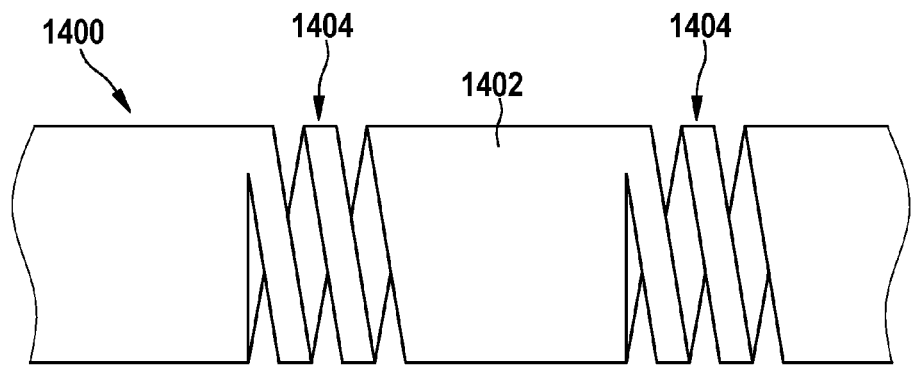
FIGS. 14A-14B are side views of a section of the electrode body of a further electrode lead according to the present description.
Figure 14B:
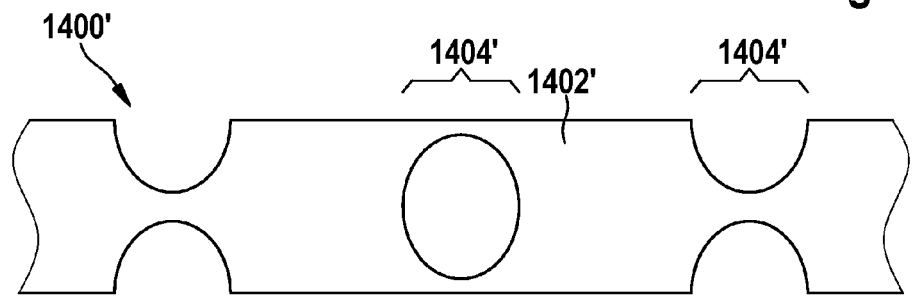

FIGS. 14A and 14B show two fundamentally different embodiments of "hard elements" for protecting an electrode lead. In both embodiments, a tube 1400 or 1400' is machined (e.g., using a laser cutting procedure or other known means) in a manner such that non-machined and therefore rigid ("hard") sections 1402 and 1402' alternate with ("soft") machined sections 1404 and 1404', which are deformed relatively easily due to the recesses created by the machining. In the embodiment depicted in FIG. 14A, soft sections 1404 are created using a strip-type incision that extends in a spiral. In the embodiment depicted in FIG. 14B, soft sections 1404' are created using circular incisions applied such that they alternate by approximately 90°, thereby ensuring that the electrode lead protected by the protective tube 1400, 1400' can bend in at least two planes.

Figure 15A:
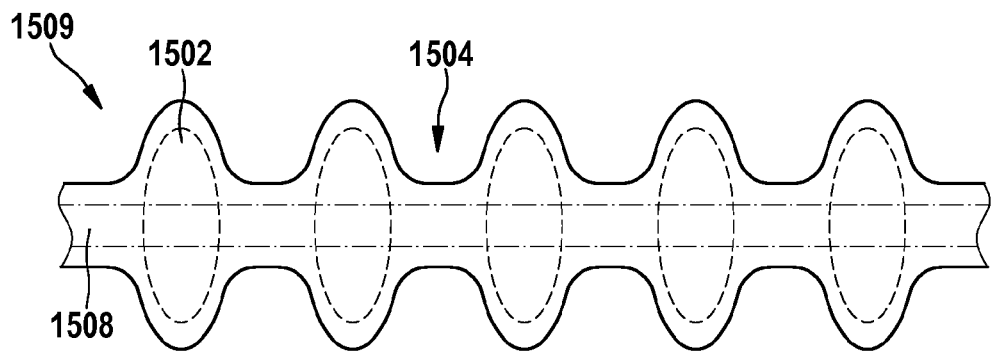
FIGS. 15A-15B are sketches of further embodiments of the electrode lead according to the present description.
Figure 15B:
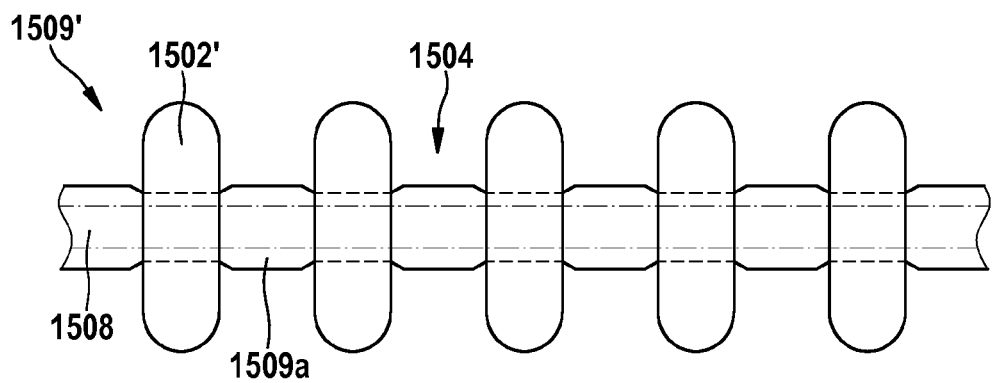

To illustrate another embodiment of the present description, FIG. 15A shows a lead body 1509 having a central lumen 1508 for receiving electrode supply leads (not depicted), which is formed by enclosing relatively greatly interspaced hard elements 1502 in a coating of an elastic mass applied by injection molding. By applying the coating via injection molding at a relatively great distance, "soft", i.e., flexurally resilient and flexibly yielding, lead body sections 1504 are formed between each of the hard elements 1502 and ensure that the final electrode lead is sufficiently flexible. FIG. 15B shows, as an alternative design having a comparable function, a lead body 1509' which is formed by pressing rounded, disk-shaped (lenticular), hard elements 1502' onto a tube 1509a comprised of a flexurally resilient and compressible material disposed at a predetermined distance from one another. In this case as well, distance ranges 1504 between hard elements 1502' are deformed relatively easily and therefore represent a type of hinged connection between the "hard" sections.

Figure 16:
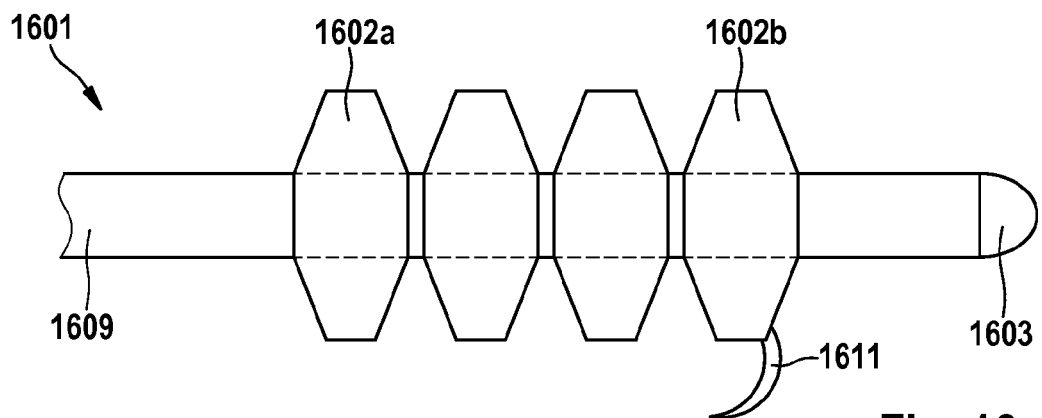
FIG. 16 is a sketch of a further embodiment of the present description.

FIG. 16 shows, in a sketch of another embodiment of the present description, a distal section of an electrode lead 1601. In the electrode lead 1601, first hard elements 1602a, which are used exclusively for protection against mechanical stress, are provided, as well as an element 1602b comprising a securing hook 1611 which can be extended after implantation. The securing hook 1611 (shown extended in FIG. 16) is controlled using a guide wire (not shown) for securing the electrode lead 1601 in the patient's bodily tissue. Element 1602b, comprising the securing hook 1611, is situated close to a distal electrode 1603 of lead 1609.

The embodiment of the present description is not limited to the above-described examples and emphasized aspects, but rather is possible in a large number of modifications that lie within the scope of a person skilled in the art. Those of skill in the art will readily appreciate that embodiments in accordance with the present invention may be implemented in a very wide variety of ways. This application is intended to cover any and all adaptations and/or variations of the embodiments discussed herein.

The terms and expressions which have been employed in the foregoing specification are used therein as terms of description and not of limitation, and there is no intention, in the use of such terms and expressions, to exclude equivalents of the features shown and/or described or portions thereof, it being recognized that the scope of the invention is defined and limited only by the claims that follow.

It will be apparent to those skilled in the art that numerous modifications and variations of the described examples and embodiments are possible in light of the above teachings of the disclosure. The disclosed examples and embodiments are presented for purposes of illustration only. Other alternate embodiments may include some or all of the features disclosed herein. Therefore, it is the intent to cover all such modifications and alternate embodiments as may come within the true scope of this invention, which is to be given the full breadth thereof. Additionally, the disclosure of a range of values is a disclosure of every numerical value within that range.

We claim:

1. An implantable electrode lead for transmitting electrical impulses to excitable bodily tissue or electrical signals tapped at bodily tissue to a detection unit or combinations thereof, the electrode lead comprising: a distal electrode; a proximal electrode contact; a lead body; and an electrode supply lead which connects the distal electrode to the proximal electrode contact and/or is used to transmit electrical shocks and/or to control sensors, and which extends in the lead body, wherein the lead body comprises a hinged alignment of closely interspaced hard elements configured and spaced for protecting the lead body and the electrode supply lead from radially acting forces and for permitting free deflection of the lead body in any direction, wherein the hinged alignment forms a rotationally symmetrical joint connection between the hard elements, wherein each hard element includes a central lumen through which the lead body and the electrode supply lead extend extends through, and wherein at least one hard element is drum-shaped and contains in an interior thereof a coil connected mechanically and electrically to the electrode supply lead, and wherein the drum-shaped element is rotatably supported on the electrode supply lead thereby enabling the lead body to rotate relative to the electrode supply lead with the coil securely placed thereon and preventing torsional stresses from forming during use of the electrode lead.

2. The electrode lead according to claim 1, wherein sections which are compressible or bendable in a flexibly yielding or flexurally resilient manner are inserted into the hinged alignment of hard elements.

3. The electrode lead according to claim 1, wherein sections which are compressible and bendable in a flexibly yielding or flexurally resilient manner are inserted into the hinged alignment of hard elements.

4. The electrode lead according to claim 1, wherein the hinged alignment of hard elements is enclosed by a flexibly yielding material, at least in sections.

5. The electrode lead according to claim 4, wherein a flexible tube is drawn over the alignment of hard elements, or they are enclosed in a coating of the flexibly yielding material.

6. The electrode lead according to claim 5, wherein the coating of flexibly yielding material is applied by injection molding.

7. The electrode lead according to claim 1, wherein the alignment of hard elements are disposed on a flexibly yielding material.

8. The electrode lead according to claim 7, wherein the alignment of hard elements are drawn or injected onto a flexibly yielding material.

9. The electrode lead according to claim 1, wherein the hard elements contain at least one of the following materials:
   a metal,
   a ceramic,
   a glass, and
   a plastic.

10. The electrode lead according to claim 9, wherein:
    the metal comprises platinum, tantalum, iridium, palladium, stainless steel, gold, or MP35N,
    the ceramic comprises Al2O3, ZrO2, TiO2, MgO, ZnO, Al2O3+TiO2, BaO+TiO2, SiC, BeO, AlN, HfC, TaC, TiN, BN, B4C, WC or Si3N4, and
    the plastic comprises PEEK, silicone, a copolymer, a polyimide, PA, high-density polyethylene or polysulphone, or variants of the aforementioned plastics filled with fibers or nanoparticles.

11. The electrode lead according to claim 1, wherein at least a few of the hard elements are directly adjacent to one another and include end faces that face one another, wherein the end faces are shaped in a manner such that tilting about a longitudinal axis of the electrode lead, which is limited relative to a minimal bending radius, is possible.

12. The electrode lead according to claim 1, wherein at least a few of the hard elements are directly adjacent to one another and are directly interconnected to each other in a tension-resistant manner using joint sections.

13. The electrode lead according to claim 1, wherein first and second hard elements which are differently shaped and additionally, or alternatively, differently sized, are enmeshed in a hinged manner.

14. The electrode lead according to claim 1, further comprising soft elements, wherein the hard and soft elements are enmeshed in a hinged manner and provided in alternating alignment.

15. The electrode lead according to claim 1, wherein the hard elements are formed by rigid sections of a tube, between which flexible sections are present which are defined by recesses formed in a wall of the tube.

16. The electrode lead according to claim 15, wherein the recesses extend in an elongated, coiled manner.

17. The electrode lead according to claim 15, wherein the recesses are designed as pairs or groups of circular or elliptical openings.

18. The electrode lead according to claim 1, wherein at least one of the hard elements contains an electrical or electronic component in a cavity provided therein configured to electrically and mechanically connect to the electrode supply lead.

19. The electrode lead according to claim 18 wherein the electrical or electronic component comprises an electrode, a coil, a sensor element, a capacitor, or an active electronic component or an electronic circuit.

20. The electrode lead according to claim 1, wherein at least one of the hard elements comprises a fixation element for mechanically fixing the electrode lead in an implanted state.

21. The electrode lead according to claim 1, wherein the hard elements include at least one central or one off-center recess, or combinations thereof, for receiving the electrode supply line or an electrode supply line.

22. The electrode lead according to claim 21, wherein at least one electrode supply lead is designed as a rope or coil insulated against the hard elements, and the recesses of the hard elements are adapted thereto.

23. The electrode lead according to claim 22, wherein an off-center recess in the hard elements is designed such that, and its alignment is selected such that, an extension of the electrode supply lead in the adjacent recesses of adjacent hard elements is predetermined, with the electrode lead extending in a coiled manner.

24. The electrode lead according to claim 1, wherein at least a few of the hard elements are directly adjacent to one another and include conical-shaped end faces that face one another, wherein a cone angle of the cone-shaped faces defines a minimal bending radius of the lead body in an area of the hard elements.

25. The electrode lead according to claim 1, wherein the hard elements are connected together by cooperating ball and socket joints.

* * * * *